(12) United States Patent
Mundy et al.

(10) Patent No.: US 6,410,512 B1
(45) Date of Patent: Jun. 25, 2002

(54) INHIBITORS OF PROTEASOMAL ACTIVITY FOR STIMULATING HAIR GROWTH

(75) Inventors: Gregory R. Mundy; I. Ross Garrett; G. Rossini, all of San Antonio, TX (US)

(73) Assignee: OsteoScreen, Inc., San Antonio, TX (US)

( * ) Notice: Subject to any disclaimer, the term of this patent is extended or adjusted under 35 U.S.C. 154(b) by 0 days.

(21) Appl. No.: 09/361,775

(22) Filed: Jul. 27, 1999

Related U.S. Application Data

(63) Continuation-in-part of application No. 09/113,947, filed on Jul. 10, 1998.

(51) Int. Cl.[7] ............................................. A61K 38/00
(52) U.S. Cl. ......................................... 514/12; 514/880
(58) Field of Search .................... 435/23, 6; 514/12, 514/44, 880; 548/453

(56) References Cited

U.S. PATENT DOCUMENTS 6,147,223 A * 11/2000 Fenteany et al. ............ 548/453

FOREIGN PATENT DOCUMENTS

| WO | WO 97/18239 | * | 5/1997 |
| WO | WO 99/43346 | * | 9/1999 |

* cited by examiner

*Primary Examiner*—Ralph Gitomer
(74) *Attorney, Agent, or Firm*—Morrison & Foerster LLP

(57) ABSTRACT

Compounds that inhibit the activity of NF-κB or inhibit the activity of the proteasome or both promote hair growth and stimulate the production of hair follicles and are thus useful in stimulating hair growth, including hair density, in subject where this is desirable.

8 Claims, No Drawings

INHIBITORS OF PROTEASOMAL ACTIVITY FOR STIMULATING HAIR GROWTH

This application is a continuation-in-part of U.S. Ser. No. 09/113,947 filed Jul. 10, 1998, the contents of which are incorporated herein by reference.

TECHNICAL FIELD

The invention relates to compositions and methods for use in enhancing hair density and growth. More specifically, the invention concerns the use of inhibitors of proteasomal activity and inhibitors of NF-κB activity for this purpose.

BACKGROUND ART

Inhibitors of proteasomal activity, and to some extent inhibitors of NF-κB activity, have two important physiological effects. First, they are able to enhance bone formation and are thus useful for treating various bone disorders. Second, they stimulate the production of hair follicles and are thus useful in stimulating hair growth, including hair density, in subject where this is desirable. The present invention focuses on this latter function.

Disorders of human hair growth include male pattern baldness, alopecia areota, alopecia induced by cancer chemotherapy and hair thinning associated with aging. These conditions are poorly understood, but nevertheless common and distressing, since hair is an important factor in human social and sexual communication.

Hair follicle regulation and growth are still not well understood, but represent dynamic processes involving proliferation, differentiation and cellular interactions during tissue morphogenesis. It is believed that hair follicles are formed only in early stages of development and not replaced.

Hardy, M. H. et al. *Trans Genet* (1992) 8:55–61 describes evidence that bone morphogenetic proteins (BMPs), members of the TGFβ super family, are differentially expressed in hair follicles during development. Harris, S. E. et al. *J Bone Miner Res* (1994) 9:855–863 describes the effects of TGFβ on expression of BMP-2 and other substances in bone cells. BMP-2 expression in mature follicles also occurs during maturation and after the period of cell proliferation (Hardy et al. (1992, supra). As noted, however, by Blessing, M. et al. *Genes and Develop* (1992) 7:204–215, the precise role functional role of BMP-2 in hair follicle maturation remains unclear.

Approaches to treat baldness abound in the U.S. patent literature. See for example U.S. Pat. No. 5,767,152 (cyanocarboxylic acid derivatives), U.S. Pat. No. 5,824,643 (keratinocyte growth factors) and U.S. Pat. No. 5,910,497 (16-pyrazinyl-substitute-4-aza-androstane 5-alpha.-reductase isozyme 1 inhibitors). There are many others.

Gat, U. et al. *Cell* (1998) 95:605–614 has demonstrated that β-catenin causes adult epithelial cells to create hair follicles, a surprising result in light of the known inability of mature cells to do so. B-Catenin is known to play a role in cell-cell adhesion and growth factor signal transfection. It is also known that after ubiquitination, β-catenin is degraded by the proteasomes. Orford, K. et al. *J Biol Chem* (1997) 272:24735–24738. At least one gene associated with hair growth (or lack thereof) has also been reported. Ahmed, W. et al. *Science* (1998) 279:720–724.

Two accepted agents currently used for the treatment of hair loss are the antihypertensive drug Minoxidil and the 5α-reductase inhibitor Finasteride. Neither is entirely satisfactory. Both suffer from modest efficacy and are inconvenient to administer. A specific, topically active and easy to administer compound with better efficacy than these agents would represent a marked advance.

The present invention discloses convenient assays for compounds that will be useful in stimulating hair growth. The assays involve inhibition of the activity of the transcription factor NF-κB or of the activity of proteasomal proteases, preferably proteasomal proteases. Compounds which inhibit these activities are generally useful in treating hair growth disorders. Compounds that inhibit the production of the transcription factor and these proteases will also be useful in the invention. Their ability to do so can be further confirmed by additional assays.

The proteasome is a noncompartmentalized collection of unrelated proteases which form a common architecture in which proteolytic subunits are self-assembled to form barrel-shaped complexes (for review, see Baumeister et al., *Cell* (1998) 92:367–380. The proteasome contains an array of distinct proteolytic activities inside eukaryotic cells. Compounds which inhibit proteasomal activity also reduce NF-κB activity by limiting its capacity to be translocated to the nucleus (Barnes, P. J. et al. *New Engl J Med* (1997) 336:1066–1071.

DISCLOSURE OF THE INVENTION

The present invention adds to the repertoire of osteogenic and hair growth stimulating agents by providing drugs which would inhibit key proteins and enzymes involved in proteasomal activity and which decrease the activity of the nuclear transcription factor NF-κB, and thus stimulate bone and hair growth. In accordance with the present invention, we have discovered that inhibition of the functions of the proteasomal proteins and the transcription factor NF-κB in bone cells leads to increased bone growth and to hair follicle formation and stimulation. Thus, assessing a candidate compound for its ability to inhibit proteasomal proteins or NF-κB provides a useful means to identify bone and hair growth anabolic agents.

The present specification thus provides methods for identification of osteogenic compounds to stimulate bone growth and compounds that stimulate hair growth by assessing their capacity to inhibit proteasome activity or to inhibit the activity of the transcription factor NF-κB, preferably to inhibit proteasomal activity. Also useful in the methods of the invention are compounds which inhibit the in situ production of the enzymes contained in the proteasome or inhibit the production of NF-κB, preferably of enzymes of the proteasomes. Once a compound found to inhibit these activities has been identified, it can be used in an additional aspect of the invention—a method to stimulate the growth of bone or of hair by contacting suitable cells with the identified compound. The cellular contact may include in vivo administration and the compounds of the invention are thus useful in treating degenerative bone diseases, fractures, dental problems, baldness, alopecia and the like. These methods are performed, according to the present invention, with compounds identified as inhibitors of proteasome activity or inhibitors of the activity of transcription factor NF-κB, preferably inhibitors of the proteasome enzymes, or inhibitors of the production of the proteasome enzymes or of NF-κB, preferably of the proteasome enzymes.

MODES OF CARRYING OUT THE INVENTION

In accordance with the present invention, there are provided methods of treating disorders of hair growth. Disorders of hair growth may be the result of a defect in the ability of existing hair follicles to extrude hair, or may be the result of a deficiency in the number of hair follicles per se. "Stimulation of hair growth" refers to increasing the volume of hair in a particular area of a subject whether this is the result of an increased rate of growth in length and/or thickness from the same number of hair follicles, growth proceeding from an enhanced number of hair follicles, or both. The number of hair follicles can be enhanced by further activating existing hair follicles or by stimulating the appearance or proliferation of hair follicles in a particular region of the skin.

As employed herein, the term "subject" embraces human as well as other animal species, such as, for example, canine, feline, bovine, porcine, rodent, and the like. It will be understood by the skilled practitioner that the subject is one appropriate to the desirability of stimulating bone growth or hair growth. Thus, in general, for example, stimulation of hair growth will be confined in most instances to animals that would appropriately exhibit such growth.

Conditions which would be benefited by "treating" or "treatment" for stimulation of hair growth include male pattern baldness, alopecia caused by chemotherapy, hair thinning resulting from aging, genetic disorders which result in deficiency of hair coverage, and, in animals, providing additional protection from cold temperatures. Thus, while use in humans may be primarily of cosmetic benefit, use in animals may be therapeutic as well.

The compositions of the invention may be administered systemically or locally. For systemic use, the compounds herein are formulated for parenteral (e.g., intravenous, subcutaneous, intramuscular, intraperitoneal, intranasal or transdermal) or enteral (e.g., oral or rectal) delivery according to conventional methods. Intravenous administration can be by a series of injections or by continuous infusion over an extended period. Administration by injection or other routes of discretely spaced administration can be performed at intervals ranging from weekly to once to three times daily. Alternatively, the compounds disclosed herein may be administered in a cyclical manner (administration of disclosed compound; followed by no administration; followed by administration of disclosed compound, and the like). Treatment will continue until the desired outcome is achieved. In general, pharmaceutical formulations will include a compound of the present invention in combination with a pharmaceutically acceptable vehicle, such as saline, buffered saline, 5% dextrose in water, borate-buffered saline containing trace metals or the like. Formulations may further include one or more excipients, preservatives, solubilizers, buffering agents, albumin to prevent protein loss on vial surfaces, lubricants, fillers, stabilizers, etc. Methods of formulation are well known in the art and are disclosed, for example, in *Remington's Pharmaceutical Sciences*, latest edition, Mack Publishing Co., Easton Pa., which is incorporated herein by reference. Pharmaceutical compositions for use within the present invention can be in the form of sterile, non-pyrogenic liquid solutions or suspensions, coated capsules, suppositories, lyophilized powders, transdermal patches or other forms known in the art. Local administration may be by injection at the site of injury or defect, or by insertion or attachment of a solid carrier at the site, or by direct, topical application of a viscous liquid, or the like. For local administration, the delivery vehicle preferably provides a matrix for the growing bone or cartilage, and more preferably is a vehicle that can be absorbed by the subject without adverse effects.

Delivery of compounds herein to wound sites may be enhanced by the use of controlled-release compositions, such as those described in PCT publication WO93/20859, which is incorporated herein by reference. Films of this type are particularly useful as coatings for prosthetic devices and surgical implants. The films may, for example, be wrapped around the outer surfaces of surgical screws, rods, pins, plates and thee like. Implantable devices of this type are routinely used in orthopedic surgery. The films can also be used to coat bone filling materials, such as hydroxyapatite blocks, demineralized bone matrix plugs, collagen matrices and the like. In general, a film or device as described herein is applied to the bone at the fracture site. Application is generally by implantation into the bone or attachment to the surface using standard surgical procedures.

In addition to the copolymers and carriers noted above, the biodegradable films and matrices may include other active or inert components. Of particular interest are those agents that promote tissue growth or infiltration, such as growth factors. Exemplary growth factors for this purpose include epidermal growth factor (EGF), fibroblast growth factor (FGF), platelet-derived growth factor (PDGF), transforming growth factors (TGFs), parathyroid hormone (PTH), leukemia inhibitory factor (LIF), insulin-like growth factors (IGFs) and the like. Agents that promote bone growth, such as bone morphogenetic proteins (U.S. Pat. No. 4,761,471; PCT Publication WO90/11366), osteogenin (Sampath et al. *Proc. Natl. Acad. Sci. USA* (1987) 84:7109–13) and NaF (Tencer et al. *J. Biomed. Mat. Res.* (1989) 23: 571–89) are also preferred. Biodegradable films or matrices include calcium sulfate, tricalcium phosphate, hydroxyapatite, polylactic acid, polyanhydrides, bone or dermal collagen, pure proteins, extracellular matrix components and the like and combinations thereof. Such biodegradable materials may be used in combination with non-biodegradable materials, to provide desired mechanical, cosmetic or tissue or matrix interface properties.

Alternative methods for delivery of compounds of the present invention include use of ALZET osmotic minipumps (Alza Corp., Palo Alto, Calif.); sustained release matrix materials such as those disclosed in Wang et al. (PCT Publication WO90/11366); electrically charged dextran beads, as disclosed in Bao et al. (PCT Publication WO92/03125); collagen-based delivery systems, for example, as disclosed in Ksander et al. *Ann. Surg.* (1990) 211(3):288–94; methylcellulose gel systems, as disclosed in Beck et al. *J. Bone Min. Res.* (1991) 6(11):1257–65; alginate-based systems, as disclosed in Edelman et al. *Biomaterials* (1991) 12:619–26 and the like.

In additional formulations, conventional preparations such as those described below may be used.

Aqueous suspensions may contain the active ingredient in admixture with pharmacologically acceptable excipients, comprising suspending agents, such as methyl cellulose; and wetting agents, such as lecithin, lysolecithin or long-chain fatty alcohols. The said aqueous suspensions may also contain preservatives, coloring agents, flavoring agents, sweetening agents and the like in accordance with industry standards.

Preparations for topical and local application comprise aerosol sprays, lotions, gels and ointments in pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise particularly sterile or sterilized products. Injectable compositions may be provided containing the active compound and any of the well known injectable carriers. These may contain salts for regulating the osmotic pressure.

If desired, the hair stimulating agents can be incorporated into liposomes by any of the reported methods of preparing liposomes for use in treating various pathogenic conditions. The present compositions may utilize the compounds noted above incorporated in liposomes in order to direct these compounds to macrophages, monocytes, as well as other cells and tissues and organs which take up the liposomal composition. The liposome-incorporated compounds of the invention can be utilized by parenteral administration, to allow for the efficacious use of lower doses of the compounds. Ligands may also be incorporated to further focus the specificity of the liposomes.

Suitable conventional methods of liposome preparation include, but are not limited to, those disclosed by Bangham, A. D. et al. *J Mol Biol* (1965) 23:238–252, Olson, F. et al. *Biochim Biophys Acta* (1979) 557:9–23, Szoka, F. et al. *Proc Natl Acad Sci USA* (1978) 75:4194–4198, Kim, S. et al. *Biochim Biophys Acta* (1983) 728:339:348, and Mayer, et al. *Biochim Biophys Acta* (1986) 858:161–168.

The liposomes may be made from the present compounds in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine, or phosphatidylinositol and the like. Synthetic phospholipids that may also be used, include, but are not limited to: dimyristoylphosphatidylcholine, dioleoylphosphatidylcholine, dipalmitoylphosphatidylcholine and distearoylphosphatidycholine, and the corresponding synthetic phosphatidylethanolamines and phosphatidylglycerols. Cholesterol or other sterols, cholesterol hemisuccinate, glycolipids, cerebrosides, fatty acids, gangliosides, sphingolipids, 1,2-bis(oleoyloxy)-3-(trimethyl ammonio)propane (DOTAP), N-[1-(2,3-dioleoyl)propyl-N,N,N-trimethylammonium chloride (DOTMA), and other cationic lipids may be incorporated into the liposomes, as is known to those skilled in the art. The relative amounts of phospholipid and additives used in the liposomes may be varied if desired. The preferred ranges are from about 60 to 90 mole percent of the phospholipid; cholesterol, cholesterol hemisuccinate, fatty acids or cationic lipids may be used in amounts ranging from 0 to 50 mole percent. The amounts of the present compounds incorporated into the lipid layer of liposomes can be varied with the concentration of the lipids ranging from about 0.01 to about 50 mole percent.

The liposomes with the above formulations may be made still more specific for their intended targets with the incorporation of monoclonal antibodies or other ligands specific for a target. For example, monoclonal antibodies to the BMP receptor may be incorporated into the liposome by linkage to phosphatidylethanolamine (PE) incorporated into the liposome by the method of Leserman, L. et al. *Nature* (1980) 288:602–604.

Veterinary uses of the disclosed compounds are also contemplated, as set forth above. Such uses would include treatment of defects associated with hair or fur in domestic animals, livestock and thoroughbred horses.

The compounds of the present invention may also be used to stimulate the growth of hair either by enhancing its rate of formation from existing follicles, stimulating inactive follicles, effecting the production of additional hair follicles or some combination of the foregoing, or by any other mechanism that may or may not presently be understood.

Within the present invention, an "effective amount" of a composition is that amount which produces a statistically significant effect. An "effective amount" for uses in stimulating hair growth is that amount which provides the desired effect in terms of length or density of hair. Such effective amounts will be determined using routine optimization techniques and are dependent on the particular condition to be treated, the condition of the patient, the route of administration, the formulation, and the judgment of the practitioner and other factors evident to those skilled in the art. General guidance for treatment regimens is obtained from experiments carried out in animal models of the disease of interest. Differences between successfully treated subjects and controls with regard to stimulation of hair growth can generally be ascertained by direct observation.

The dosage of the compounds of the invention will vary according to the extent and severity of the need for treatment, the activity of the administered compound, the general health of the subject, and other considerations well known to the skilled artisan. Generally, they can be administered to a typical human on a daily basis as an oral dose of about 0.1 mg/kg-1000 mg/kg, and more preferably from about 1 mg/kg to about 200 mg/kg. The parenteral dose will appropriately be 20–100% of the oral dose. While oral administration may be preferable in most instances where the condition is a bone deficit (for reasons of ease, patient acceptability, and the like), alternative methods of administration may be appropriate for selected compounds and selected defects or diseases. While topical administration is generally preferable for stimulating hair growth, as generally only local effects are desired, systemic treatment may be preferable in some instances as well.

Assays for Compounds Useful in the Invention

Assays for assessing the ability of a compound to inhibit proteasomal activity and for inhibitors of NF-κB activity are well known in the art. Two typical, but nonlimiting assays are described below.

Assessment of Proteasomal Activity

Proteasomal activity is measured by an increase in cytoplasmic ubiquitinylated protein complexes, as assessed by Western blotting using an anti-ubiquitin antibody.

MG-63 cells are grown in confluency in alpha MEM media and 10% fetal calf serum (FCS). Cells are then treated for 24 hours with specific compounds. Following the indicated treatments, cells are scraped with a disposable scraper, washed twice with phosphate saline solution (137 mM NaCl, 10 mM d-glucose, 4 mM KCl, 0.5 mM $Na_2HPO_4$, 0.1 mM $KH_2PO_4$), centrifuged, and the resulting pellet is suspended in the sample buffer containing 2% SDS, pH 6.75. The samples are heated and the concentration of total protein calculated by means of Micro bicinchoninic acid (BCA) Protein Assay Kit (Pierce, Rockford, Ill./USA). The samples are diluted to obtain a final protein concentration of 2 mg/ml, supplemented with 10% 2-mercaptoethanol, 1% bromophenol blue and run on a 4–15% SDS-PAGE. Resulting gels are Western blotted with anti-ubiquitin rabbit polyclonal antibody (diluted 1:100; Sigma, St. Louis, Mo./USA). The samples are visualized with horse-radish peroxidase coupled anti-rabbit IgG antibodies (Amersham Corp., Arlington Heights, Ill./USA) using ECL detection kits (Amersham Corp.).

NF-κKB Activity Assays

Cells are treated with different concentrations of compounds, and nuclear extracts prepared. Briefly, cells are washed with phosphate-buffered saline, and resuspended in lysis buffer (0.6% Nonidet P-40, 150 mM NaCl, 10 mM Tris-HCl, pH 7.9, 1 mM EDTA, 0.5 mM DTT and a cocktail of protease inhibitors (Complete (TM), Boehringer Mannheim). After incubation on ice for 15 min, nuclei are collected by centrifugation. The pellet is resuspended in nuclear extraction buffer (10 mM Hepes, pH 7.9, 420 mM NaCl, 0.1 mM EDTA, 1.5 mM NgCl$_2$, 0.5 mM DTT, protease inhibitors (Complete (TM), Boehringer Mannheim), 25% glycerol), and incubated at 4 degrees C. for 30 min. The supernatant is collected and dialyzed in a buffer containing 10 mM Tris0HCl, pH 7.5, 50 mM NaCl, 5 mM MgCl$_2$, 1 mM EDTA, 1 mM DTT, and 20% glycerol. After dialysis, the nuclear extract is centrifuged to remove precipitated proteins, and aliquots are stored at −70 C. Protein concentration in the nuclear extracts is measured by the method of Bradford using a dye-binding assay kit (Bio-Rad).

The probe for electrophoretic mobility shift assays is a $^{32}$P-labeled double-stranded oligonucleotide containing the consensus sequence specific for NF-κB (Promega). Nuclear extracts (5 μg) are pre-incubated in 20-ul reaction mixtures containing 10 mM Tris-HCl, pH 7.5, 50 mM NaCl, 2.5 mM DTT, 0.5 mM EDTA, 1 mM MgCl$_2$, 4% glycerol, and 5 μg of poly (dI-dC). After 10 min at room temperature, 10–20 fmol of probe is added, and incubated further for 20 min. DNA-protein complexes are separated from free oligonucleotides on a 5% polyacrylamide/0.5×TBE gel (45 mM Tris-HCl, 45 mM boric acid, 1 mM EDTA). After electrophoresis, gels are dried and autoradiographed.

Assays for Production Inhibition

Compounds which inhibit the production of the enzymes having proteasomal activity or of NF-κB can be assessed by measuring the level of production of these proteins in the presence and absence of candidate compounds. The levels of production can be readily measured in in vitro systems using, for example, immunoassays for the level of protein produced. The levels of such proteins can also be assessed by utilizing, for example, methionine labeling and size separation of proteins in the cells to be assessed. In order to effect a convenient level of protein production for measurement, it is advantageous to use recombinant expression systems for the relevant enzymes or the NF-κB so that substantial amounts are produced.

Typical approaches to inhibiting the production of NF-κB or proteasome enzymes include the use of antisense technology or formation of triplexes with double-stranded forms of nucleotide sequences relevant in the expression of the genes. In addition, various small molecules may also inhibit this production.

Assay for Hair Growth

The ability of the compositions of the invention to stimulate hair growth was, surprisingly, discovered in the course of assessing their ability to stimulate the growth of bone. Accordingly, set forth below is the bone growth assay that led to the discovery of the hair growth stimulating ability of these compounds.

In vivo Assay of Effects of Compounds on Murine Calvarial Bone Growth

Male ICR Swiss white mice, aged 4–6 weeks and weighing 13–26 gm, are employed, using 4–5 mice per group. The calvarial bone growth assay is performed as described in PCT application WO95/24211, incorporated by reference. Briefly, the test compound or appropriate control vehicle is injected into the subcutaneous tissue over the right calvaria of normal mice. Typically, the control vehicle is the vehicle in which the compound was solubilized, and is PBS containing 5% DMSO or is PBS containing Tween (2 μl/10 ml). The animals are sacrificed on day 14 and bone growth measured by histomorphometry. Bone samples for quantitation are cleaned from adjacent tissues and fixed in 10% buffered formalin for 24–48 hours, decalcified in 14% EDTA for 1–3 weeks, processed through graded alcohols; and embedded in paraffin wax. Three to five μm sections of the calvaria are prepared, and representative sections are selected for histomorphometric assessment of the effects on bone formation and bone resorption. Sections are measured by using a camera lucida attachment to trace directly the microscopic image onto a digitizing plate. Bone changes are measured on sections cut 200 μm apart, over 4 adjacent 1×1 mm fields on both the injected and noninjected sides of the calvaria. New bone is identified by its characteristic woven structure, and osteoclasts and osteoblasts are identified by their distinctive morphology. Histomorphometry software (OsteoMeasure, Osteometrix, Inc., Atlanta) is used to process digitizer input to determine cell counts and measure areas or perimeters.

Typical treatment regimens for testing utilize application of the compound to be tested over several days of repeated administration.

Hair Growth: In Vivo Assay of Effects of Compounds on Hair Follicles Proliferation and Hair Growth The assay described above to assess the effect of compounds on calvarial bone growth can also be used to assess the ability of compounds to stimulate hair growth. The test compound or appropriate control vehicle is applied to the upper and lower back of male ICR Swiss white mice either topically or by subcutaneous injection. The vehicle is selected as appropriate for the compound to be tested and for the route of administration. Optionally, the hair in the test area may be removed prior to administration. After a suitable interval, typically 7 days, the mice are anesthetized and a biopsy of the dorsal treatment area is taken using a 6 mm dermal punch. The specimens are fixed in 10% buffered formalin and imbedded in paraffin wax, and sectioned and stained to observe hair follicles. In addition, photography can be used to observe and record hair growth; typically such growth is observed after 14–18 days. After a suitable interval, typically 21 days, the animals may be euthanized and the hair analyzed for fiber analysis and the tissue from the treatment area analyzed for quantitation of hair follicles.

Nature of the Compounds Useful in the Invention

The compounds useful in the methods and compositions of the invention are inhibitors of proteasomal activity, of the transcription factor NF-κB, preferably both. Known inhibitors of these activities can be ascertained from the literature or compounds can be tested for these activities using assays known in the art. In addition, inhibitors which lower the level of effective expression of the nucleotide sequence encoding the enzymes that have proteasomal activity or of the nucleotide sequence encoding NF-κB can be assessed and used in the invention methods.

Compounds known to be proteasome or NF-κB inhibitors include:

| | Proteasome Inhibitors |
|---|---|
| PSI | N-carbobenzoyl-Ile-Glu-(OtBu)-Ala-Leu-CHO |
| MG-132 | N-carbobenzoyl-Leu-Leu-Leu-CHO |
| MG-115 | N-carbobenzoyl-Leu-Leu-Nva-CHO |
| MG-101 or Calpain Inh I | N-Acetyl-Leu-Leu-norLeu-CHO |
| ALLM | N-Acetyl-Leu-Leu-Met-CHO |
| | N-carbobenzoyl-Gly-Pro-Phe-Leu-CHO |
| | N-carbobenzoyl-Gly-Pro-Ala-Phe-CHO |
| | N-carbobenzoyl-Leu-Leu-Phe-CHO |
| | N-carbobenzoyl-Leu-Ala-Leu-CHO |
| Gliotoxin | 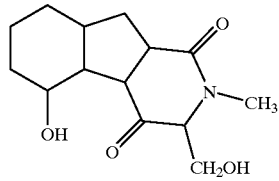 |
| SN50 | NLS of NF-κB MW 2781 |
| Bay 11-7082 | 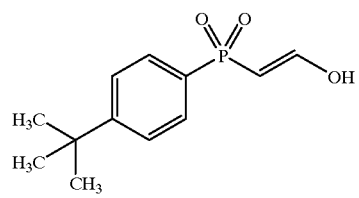 |
| Capsaicin | 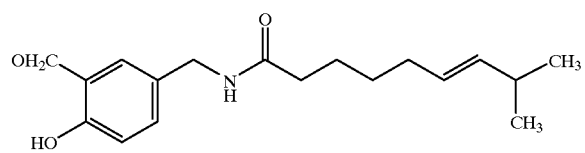 |
| PDTC | 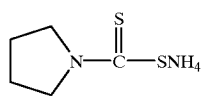 |
| Simvastatin | 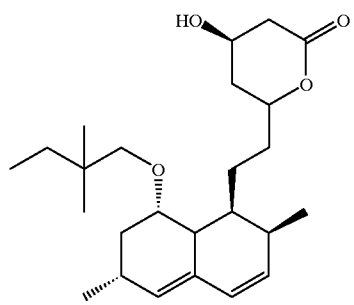 |

-continued

Proteasome Inhibitors

ALLN

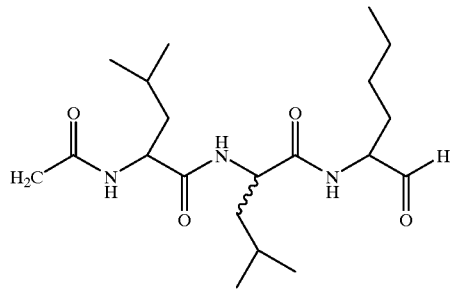

N-Acetyl-Leu-Leu-Nle-CHO

MG-262

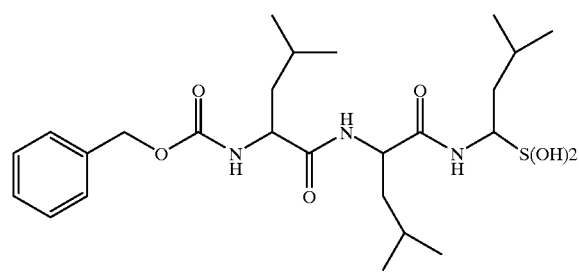

PPM-18

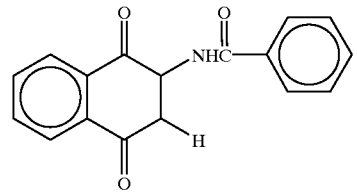

Cyclosporin A

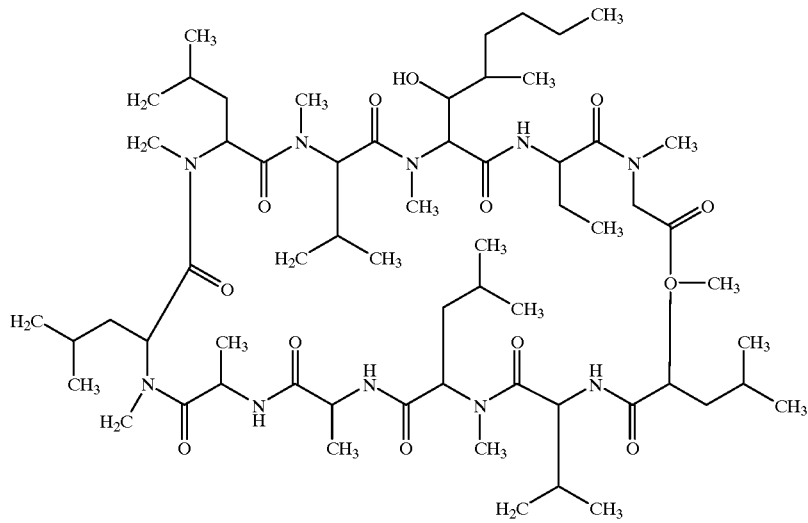

See, for example, Vinitsky, A. et al. *J Biol Chem* (1994) 269:29860–29866; Figueiredo-Pereira, M. E. et al. *J Neurochem* (1994) 63:1578–1581; Wojcik, C. et al. *Eur J Cell Biol* (1996) 71:311–318.

In the foregoing list, lactacystin is known to be an irreversible inhibitor of proteasome activity. It binds to the μ catalytic subunit and is a specific inhibitor of the 20S proteasome. It also irreversibly inhibits NF-κB.

SN50 is the NLS (nuclear localization sequence) of p50 plus the hydrophobic region of K-FGF. It inhibits the translocation of the NF-κB active complex to the nucleus.

Certain peptidyl epoxy ketones such as EST are irreversible inhibitors of the proteasomes. MG-132 shows activity against the chymotryptic activity of the 20S protein without affecting its ATPase or isopeptidase activity and reversibly inhibits NF-κB activity. MG-115 and MG-341 show similar activities to MG-132. Various other inhibitors of NF-κB are less active in the ABA assay. These include capsaicin, curcumin, and resiniferatoxin. Other compounds known to inhibit NF-κB are gliotoxin and PDTC (1-pyrrolidine carbothiotic acid). Various other compounds such as BAY-11-7082 and BAY-11-7085 as well as calyculin-A inhibit phosphorylation of NF-κB. Calpain inhibitor inhibits calpain 1 and the proteasome; other compounds such as olomoucine and roscovitine inhibit cdk2 and/or cdk5.

An additional compound shown to be a proteasome inhibitor is pentoxyfilline (PTX). Combaret, L. et al. *Mol Biol Rep* (1999) 26:95–101. It is active in the in vitro calvarial assay described above.

The following examples are intended to illustrate but not to limit the invention.

EXAMPLE 1

Effect of PSI and Other Proteasome Inhibitors on Hair Follicle Production

The in vivo bone calvarial growth assay of Example 3 was modified to observe the number of hair follicles in treated mice. In initial observations, PSI (5 mg/kg/day) was injected three times a day for 5 days over the calvaria of Swiss ICR mice as described above. Sixteen days later the mice were sacrificed. Histology of the calvaria revealed a strikingly large increase in the number of hair follicles in those mice treated with PSI versus control mice. In addition to PSI, MG132 (10 mg/kg), MG115 (10 mg/kg) and lactacysin administered in the same way also stimulated an increase in the number of hair follicles.

EXAMPLE 2

Stimulation of Hair Growth

Male Swiss ICR mice were first treated to remove hair from the scalp and dorsal regions as follows. Paraffin wax was liquefied by heating to 55° C. and the liquefied wax then applied by brush to the scalp and/or back (under anesthesia). The wax was allowed to solidify and then removed. The day following hair stripping, PSI (1 mg/kg/day) was injected subcutaneously three times a day for five days into the scalp and dorsal region. On day 7 a dermal punch biopsy was taken; histology revealed a large increase in the number of hair follicles in mice administered PSI versus control mice. By day 18, it was observable that the treated mice had a hair growth rate greater than that of the mice in the control group.

The mice were sacrificed on day 21 and histology was performed on the dermis of the scalp and of the dorsal region. In the treated mice, mature hair follicles in numbers much greater than in controls had migrated to the lower region of the dermis. Upon closer examination, it was observed that mice that had received only vehicle had quiescent hair follicles. When treated with PSI such follicles were stimulated to differentiate into mature hair follicles and to migrate to the lower region of the dermis.

EXAMPLE 3

Topical Administration

PSI was prepared as a topical formulation, where the vehicle was 50% propylene glycol, 30% ethanol, 20% deionized water, at 0.1% concentration of PSI. The solution was applied 3 times a day for 5 days. The mice in a treated group were observed as compared to controls similarly treated with vehicle alone. The results at day 16 showed stimulation of hair growth relative to the controls.

In addition to stimulating hair growth, PSI was able to thicken both the hair and the hair shaft. PSI increases hair count when the follicle area is greater than 0.01 mm². When the protocol above was repeated using a 0.5% solution of PSI in groups containing 5 mice each, the number of hairs per 0.8 mm² was 60 in the treated mice versus about 10 in the control group. The percentage of follicle area in a region of about 0.8 mm² was about 30% as an average in the treated group as compared to 15% as an average in the control group.

EXAMPLE 4

Dose Requirements

In order to determine the minimal effective dosage of PSI, when used topically, a dose response curve for PSI was prepared. All experiments were preformed according to current good laboratory practice regulations (21CFR58). The mice were divided into 7 groups, 10 mice each, wherein one group was control treated only with vehicle and groups 1–6 with a series of increasing concentrations of PSI in a vehicle comprising 50% propylene glycol, 30% ethanol, 20% deionized water. The concentrations were 0.006%, 0.012%, 0.025%, 0.05%, 0.11% and 0.5%.

The mice were anesthetized (50 μl Mouse Cocktail containing 3 ml ketamine, 2 ml small animal rompum, 5 ml NaCl), identified by ear punch code, weighed and the hair on the dorsal side removed by waxing as described in Example 6. After waxing, the animals were photographed. On the following day (day 1), 100 μl of PSI at the above concentrations in vehicle was brushed onto the area of removed hair. A similar application of PSI solution was performed daily for an additional 4 days.

On Day 7 mice were anesthetized and a biopsy of the dorsal treatment area taken using a 6 mm dermal punch; the specimens were fixed in 10% buffered formalin and embedded in paraffin wax. Sections were cut using a standard microtome.

Mice were monitored daily for signs of hair growth, and any hair growth was recorded by photography. On day 21 animals were euthanized (75 mg/kg body weight phenobarbital, IP injection), 2 cm hair samples were taken for optical based fiber analysis, and the remaining dorsal treatment area was fixed in 10% buffered formalin for further histological analysis. Analysis included quantification of hair thickness and quantification of mature hair follicles. Results were expressed as the mean=+/−the standard error of the mean. Data were analyzed by repeated measures of analysis of variance followed by the Tukey-Kramer post test P values of <0.05 were considered significant.

The results indicate that the minimal effective dose of PSI is 0.5% applied 1 time a day for 4 days; additional experiments showed that 0.1% of PSI applied topically 3 times a day for 5 days was also effective.

Gross observation of mice receiving an effective dose indicated an enhanced rate of hair growth, a thickening of hair diameter, increase in sheath diameter, and differentiation of quiescent hair follicles into more mature forms.

The contents of all documents cited above are expressly incorporated herein to the extent required to understand the invention.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method to treat a mammalian subject for a condition benefited by stimulating hair growth which method comprises administering to said mammalian subject in need of such treatment an effective amount of N-carbobenzoyl-Ile-Glu-(OtBu)-Ala-Leu-CHO (PSI).

2. The method of claim 1, wherein said subject is a human.

3. The method of claim 1, wherein said condition to be treated is selected from the group consisting of male pattern baldness, alopecia caused by chemotherapy, hair thinning due to aging, and genetic disorders.

4. The method of claim 1, wherein said subject is a non-human mammal.

5. The method of claim 4, wherein said hair growth provides additional protection from cold temperatures.

6. The method of claim 1, wherein said hair growth is due to thickened hair sheath diameter, increased hair diameter, differentiation of quiescent hair follicles into more mature forms, increased rate of growth in hair length and/or thickness, or the appearance of proliferation of new hair follicles.

7. The method of claim 1, wherein said compound is co-administered with an agent promoting skin tissue growth or infiltration.

8. The method of claim 7, wherein said agent is selected from the group consisting of an epidermal growth factor, a fibroblast growth factor, a platelet-derived growth factor, a transforming growth factor, a parathyroid hormone, a leukemia inhibitory factor, and an insulin-like growth factor.

* * * * *